US010966949B2

(12) United States Patent
Dattilo et al.

(10) Patent No.: US 10,966,949 B2
(45) Date of Patent: Apr. 6, 2021

(54) DIETARY SUPPLEMENTATION TO ACHIEVE OXY-REDOX HOMEOSTASIS AND EPIGENETIC STABILITY

(71) Applicant: PARTHENOGEN SAGL, Lugano (CH)

(72) Inventors: Maurizio Dattilo, Montagnola (CH); Yves Menezo, Caluire (FR)

(73) Assignee: PARTHENOGEN SAGL, Lugano (CH)

( * ) Notice: Subject to any disclaimer, the term of this patent is extended or adjusted under 35 U.S.C. 154(b) by 359 days.

(21) Appl. No.: 15/762,763

(22) PCT Filed: Oct. 7, 2016

(86) PCT No.: PCT/EP2016/073942
§ 371 (c)(1),
(2) Date: Mar. 23, 2018

(87) PCT Pub. No.: WO2017/060391
PCT Pub. Date: Apr. 13, 2017

(65) Prior Publication Data
US 2020/0237701 A1    Jul. 30, 2020

(30) Foreign Application Priority Data
Oct. 7, 2015   (WO) ................. PCT/EP2015/073108

(51) Int. Cl.
| | |
|---|---|
| *A61K 31/205* | (2006.01) |
| *A23L 33/175* | (2016.01) |
| *A23L 33/15* | (2016.01) |
| *A61K 9/20* | (2006.01) |
| *A61K 31/198* | (2006.01) |
| *A61K 31/4406* | (2006.01) |
| *A61K 31/4415* | (2006.01) |
| *A61K 31/455* | (2006.01) |
| *A61K 31/525* | (2006.01) |
| *A61K 31/714* | (2006.01) |
| *A61K 33/30* | (2006.01) |

(52) U.S. Cl.
CPC ............ *A61K 31/205* (2013.01); *A23L 33/15* (2016.08); *A23L 33/175* (2016.08); *A61K 9/2004* (2013.01); *A61K 31/198* (2013.01); *A61K 31/4406* (2013.01); *A61K 31/4415* (2013.01); *A61K 31/455* (2013.01); *A61K 31/525* (2013.01); *A61K 31/714* (2013.01); *A61K 33/30* (2013.01)

(58) Field of Classification Search
CPC ...... A61K 31/205; A23L 33/15; A23L 33/175
See application file for complete search history.

(56) References Cited

U.S. PATENT DOCUMENTS

| 5,597,585 | A | 1/1997 | Williams et al. |
|---|---|---|---|
| 2002/0182196 | A1 | 12/2002 | McCleary |
| 2005/0171034 | A1 | 8/2005 | Halevie-Goldman |
| 2007/0065456 | A1 | 3/2007 | Woods |
| 2007/0116779 | A1 | 5/2007 | Mazzio |
| 2017/0035879 | A1* | 2/2017 | Morgan ................. A61K 33/06 |

FOREIGN PATENT DOCUMENTS

| DE | 102007053369 A1 | 7/2009 |
|---|---|---|
| EP | 0891719 A1 | 1/1999 |
| WO | 2005/067972 A1 | 7/2005 |
| WO | 2014/025905 A1 | 2/2014 |

OTHER PUBLICATIONS

Aşlar, Deniz et al., "Prevalence of MTHFR, MTR and MTRR Gene Polymorphisms in Turkish Patients with Nonsyndromic Cleft Lip and Palate", Gene Therapy and Molecular Biology, vol. 16, Jul. 18, 2014, pp. 115-129.
Banerjee, Ruma "Redox outside the Box: Linking Extracellular Redox Remodeling with Intracellular Redox Metabolism", The Journal of Biological Chemistry, vol. 287, No. 7, Feb. 10, 2012, pp. 4397-4402.
Boyles, Abee L. et al., "Neural Tube Defects and Folate Pathway Genes: Family-Based Association Tests of Gene-Gene and Gene-Environment Interactions", Environmental Health Perspectives, vol. 114, No. 10, Oct. 2006, pp. 1547-1552.
Ereno-Orbea, June et al., "Structural insight into the molecular mechanism of allosteric activation of human cystathionine β-synthase by S-adenosylmethionine", PNAS, Sep. 2, 2014, pp. E3845-E3852.
Frye, Richard E. et al., "Treatments for biomedical abnormalities associated with autism spectrum disorder", Frontiers in Pediatrics, vol. 2, Art. 66, Jun. 2014, pp. 1-8.
Ganguly, Paul et al., "Role of homocysteine in the development of cardiovascular disease", Nutrition Journal, Jan. 10, 2015, pp. 1-10.
Gerstein, Hertzel C. et al., "Effects of Intensive Glucose Lowering in Type 2 Diabetes", The New England Journal of Medicine, vol. 358, No. 24, Jun. 12, 2008, pp. 2545-2559.

(Continued)

*Primary Examiner* — Pancham Bakshi
(74) *Attorney, Agent, or Firm* — Perkins Coie LLP; Viola T. Kung

(57) ABSTRACT

The invention describes pharmaceutical, dietary and/or food compositions, preferably dietary supplements, exerting the ability to activate the endogenous antioxidant system by feeding essential micronutrients to both the one carbon cycle and the trans-sulfuration pathway so to achieve effective oxy-redox homeostasis together with an improved energy balance and healthy processes of cell growth and differentiation including DNA methylation and epigenetic regulation.
The invention further relates to the use of the aforementioned compositions to decrease homocysteine levels and for the support to menopause, pregnancy and reproductive competence and for the prevention and/or treatment of diabetes, celiac disease, neurodegenerative diseases, cardiovascular diseases, Autism Spectrum Disorders (ASD) or Neurodevelopmental Disorders.

17 Claims, No Drawings

(56) References Cited

OTHER PUBLICATIONS

James, S. J. et al., "Metabolic biomarkers of increased oxidative stress and impaired methylation capacity in children with autism", Am J Clin Nutr, 80, Aug. 23, 2004, pp. 1611-1617.

Johnson, Amy R. et al., "Deletion of murine choline dehydrogenase results in diminished sperm motility", FASEB J. Aug. 2010; 24(8):pp. 2752-2761.

Klaunig, James E. et al., "Oxidative Stress and Oxidative Damage in Carcinogenesis", Toxicologic Pathology, vol. 38, 2010, pp. 96-109.

O'Hagan, Heather M. et al., "Oxidative Damage Targets Complexes Containing DNA Methyltransferases, SIRT1 and Polycomb Members to Promoter CpG Islands", Cancer Cell 20, Nov. 15, 2011, pp. 606-619.

Robien, Kim et al., "Methylenetetrahydrofolate Reductase Genotype Affects Risk of Relapse after Hematopoietic Cell Transplantation for Chronic Myelogenous Leukemia", Clinical Cancer Research, vol. 10, Nov. 15, 2004, pp. 7592-7598.

Tsai, Michael Y. et al., "High Prevalence of a Mutation in the Cystathionine β-Synthase Gene", Am. J. Hum. Genet. vol. 59: 1996, pp. 1262-1267.

Ulrich, Cornelia M. et al., "Folate Supplementation: Too Much of a Good Thing?", Cancer Epidemiol Biomarkers Prev, vol. 15(2), Feb. 2006, pp. 189-193.

Van Der Put, Nathalie M. et al., "A Second Common Mutation in the Methylenetetrahydrofolate Reductase Gene: An Additional Risk Factor for Neural-Tube Defects?", Am. J. Hum. Genet., Am. J. Hum. Genet. 62:000-000, Apr. 10, 1998, 8 pages.

Watkins, David et al., "Hyperhomocysteinemia Due to Methionine Synthase Deficiency, cblG: Structure of the MTR Gene, Genotype Diversity, and Recognition of a Common Mutation, P1173L", Am. J. Hum. Genet. 71:143-153, May 30, 2002, pp. 143-153.

Wu, Jinfang et al., "Alzheimer's disease (AD) like pathology in aged monkeys following infantile exposure to environmental metal lead (Pb): Evidence for a developmental origin and environmental link for AD", J Neurosci. Author manuscript; available in PMC 2008 Jul. 28, 2008, pp. 1-18.

Yang, Quan-He et al., "Prevalence and effects of gene-gene and gene-nutrient interactions on serum folate and serum total homocysteine concentrations in the United States: findings from the third National Health and Nutrition Examination Survey DNA Bank", Am J Clin Nutr, vol. 88, Mar. 17, 2008, pp. 232-246.

Zappacosta, Bruno et al., "Genotype Prevalence and Allele Frequencies of 5,10-Methylenetetrahydrofolate Reductase (MTHFR) C677T and A1298C Polymorphisms in Italian Newborns", LabMedicine, vol. 40, No. 12, Dec. 2009, pp. 732-736.

Zawia, Nasser H. et al., "Epigenetics, oxidative stress and Alzheimer's Disease", NIH Public Access, Free Radic Biol Med, Author manuscript; available in PMC 2010 May 1, pp. 1-18.

Zheng, Zhanjie et al., "Correlation between Behavioural and Psychological Symptoms of Alzheimer Type Dementia and Plasma Homocysteine Concentration", BioMed Research International vol. 2014, Jun. 4, 2014, pp. 1-6.

International Search Report dated Nov. 25, 2016 in International Application No. PCT/EP2016/073942.

International Search Report dated Nov. 30, 2015 in International Application No. PCT/EP2015/073108.

* cited by examiner

DIETARY SUPPLEMENTATION TO ACHIEVE OXY-REDOX HOMEOSTASIS AND EPIGENETIC STABILITY

This application is a National Stage of International Application PCT/EP2016/073942, filed Oct. 7, 2016, published Apr. 13, 2017, under PCT Article 21(2) in English; which claims the priority of International Application No. PCT/EP2015/073108, filed Oct. 7, 2015. The contents of the above-identified applications are incorporated herein by reference in their entireties.

The present invention relates to pharmaceutical, dietary and/or food compositions, preferably dietary supplements, exerting the ability to activate the endogenous antioxidant system by feeding essential micronutrients to both the one carbon cycle and the trans-sulfuration pathway so to achieve effective oxy-redox homeostasis together with an improved energy balance and healthy processes of cell growth and differentiation including DNA methylation and epigenetic regulation.

The invention further relates to the use of the aforementioned compositions to decrease homocysteine levels and for the support to menopause, pregnancy and reproductive competence and for the prevention and/or treatment of diabetes, celiac disease, neurodegenerative diseases, cardiovascular diseases, Autism Spectrum Disorders (ASD) or Neurodevelopmental Disorders.

BACKGROUND

Oxidative stress may be defined as an imbalance between the total load of reactive oxygen species, both endogenous and exogenous, and the antioxidant capability of the cells, which is based on the occurrence of a series of enzymatic and non-enzymatic antioxidant substances, all of them venerated and re-generated by or relying on the availability of reduced glutathione (GSH) as the universal cellular source of reducing equivalents.

The oxidative imbalance is caused by a complex framework of contributing factors including excessive load of pro-oxidants due to passive environmental exposure, to toxic substances and/or to wrong habits (e.g. smoking) on one side and defective defenses due to bad and irregular feeding on the other side. The individual genetic substrate may also contribute to an increased susceptibility to the oxidative damages.

Whatever the origin, oxidative stress is responsible of molecular damages to many cellular macromolecules including proteins, lipids and DNA. This causes direct metabolic perturbations and endocrine derangements and has been linked to an increased risk of suffering from a series of problems including, but not limited to, infertility and congenital malformations and malfunctions, complex metabolic diseases, cardiovascular and neurologic degeneration.

The clinical relevance of oxidative stress triggers the need of corrective interventions starting from avoidance of toxic exposures and from a balanced diet ensuring adequate availability of natural antioxidants. However major changes of the lifestyle are often difficult to achieve and to keep in the long run and it is common practice to integrate the diet with the ingestion of nutritional formulations containing enzymatic and/or non-enzymatic antioxidants. This is aimed at artificially increasing the redox power of the intracellular environment so to antagonize the effects of pro-oxidants. Enzymatic direct antioxidants are enzymes that contribute to the reductive reactions such as, among the others, super oxide dismutases (SOD) and catalase. Non enzymatic direct antioxidants are substances acting as an oxidation substrate that gets oxidized while another (toxic) substance is reduced. Typical but non exclusive examples are Vitamins A, C, and E, selenium and CoQ 10.

The supplementation with antioxidants is however hampered by a series of problems. First, once the reductive reaction occurs, each of these antioxidants directly or indirectly generates secondary pro-oxidants whose reactivity and metabolic fate is often difficult to predict, especially when used as part of a complex mixture of these molecules. Second, whatever the composition, an antioxidant cocktail suitable for human use will have to contain a finite number of substances. These substances will influence an as well finite number of oxy-redox reactions that may be imbalanced to the opposite and as well pathologic reductive stress whereas all the other oxy-redox reactions will remain under oxidative stress. The final outcome is a reductive stress in selected pathways and unmodified oxidative stress in the others with no chances to achieve an oxy-redox balance. This explains why, in spite of reliable in vitro models of pro-oxidants antagonization, the clinical outcomes from antioxidants supplementations are absent or partial or difficult to demonstrate.

Oxidative stress is also known to associate to an increased release of the molecule homocysteine possibly leading to high blood levels. Homocysteine is the end-product of transmethylation reactions and requires dietary folates to be re-cycled to methionine. High circulating homocysteine has been linked to the risk of cardiovascular, metabolic and degenerative disease and very high levels may increase the risk of thrombotic events.

In addition, chronic oxidative stress associates to genetic and epigenetic instability, even though the precise underlying mechanisms have not yet been fully elucidated. As a matter of fact in vitro and in vivo models clearly indicate that under chronic oxidative insult there is a higher frequency of DNA mutations (Klaunig J. E. et al.: *Oxidative Stress and Oxidative Damage in Carcinogenesis. Toxicologic Patholology* 2010; 38: 96-109) causing genetic instability. More commonly, and possibly more important, chronic oxidative stress associates with an alteration of DNA methylation and of the profile of gene expression configuring a so-called epigenetic instability (O'Hagan H. M. et al.: *Oxidative Damage Targets Complexes Containing DNA Methyltransferases, SIRT1, and Polycomb Members to Promoter CpG islands. Cancer Cell* 2011; 20, 606-619). The transcription of many genes is indeed regulated by a variety of mechanisms of repression or activation of the gene promoters that are based on chemical modifications of DNA and of the DNA nursing proteins, mainly the histones. These chemical modifications include, among others, phosphotylation, acetylation, ubiquitation and sumoylation. However, the actual massive primer of all these DNA re-arrangements is the extensive methylation of the DNA that occurs at cytosine residues to form methyl-cytosine. In particular, methylation occurs at sequences of the DNA that are enriched of cytosine-phosphate binding-guanosine (CpG) repeats called CpG islands. A derangement of the DNA methyloma is commonly observed as a consequence of chronic oxidative stress in many models of degenerative (Zawia N. H. et al.: *Epigenetics, oxidative stress and Alzheimer's Disease. Free Radic Biol Med* 2009; 46(9): 1241-1249) and neoplastic diseases (*Cancer Cell* 2011; 20, 606-619). The resulting dysregulation in gene transcriptions induces a chaotic phenotype that may cause or worsen or complicate diseases. In particular it is considered to be a cause of neural tube defects (NTD), mainly spina bifida, and of autism spectrum diseases (ASD) in the newborns. Indeed, DNA methylation and epigenetic marking depend on dietary folates and folate supplementation is effective in reducing the incidence of epigenetic-related disease such as NTDs and ASDs.

Both high homocysteine and epigenetic problems, i.e. the methylation imbalance, are always been considered as independently associated to oxidative stress and this is the main reason for the empiric inclusion into many antioxidants cocktails of folic acid, B vitamins, and other substances known to contribute to the metabolism of homocysteine and to DNA methylation. All these substances are not antioxidant per se but, given their positive contribution to the metabolism of homocysteine and to DNA methylation/epigenetic, their inclusion into antioxidant treatments was assumed as a completion adding further benefits.

This is the case of the patent application WO 2005/067972 A1 (Kaiser 2005). Kaiser discloses a nutritional composition including:

1) at least one vitamin antioxidant selected among vitamin C, bioflavonoid complex and vitamin E;
2) at least one mineral antioxidant selected between zinc and selenium, or both;
3) at least 3 high potency antioxidants selected among alpha lipoic acid, acetyl L-carnitine, N-acetyl cysteine, co-enzyme Q10 and glutathione (GSH).

Besides the above list of substances Kaiser 2005 also mentioned the possible inclusion in the claimed nutritional composition of a long list of substances including, among others, vitamins or minerals. According to the description of the invention these substances were "useful to promote efficiency of their respective processes as well as augment the functioning of the antioxidant nutrients of the invention". Inasmuch, these added substances were clearly intended as ancillary substances possibly enlarging the positive effect of the nutritional composition whose antioxidant activity remained based on the substances listed here above at points 1) to 3).

Moreover, the role of these ancillary substances as direct and main effectors of the antioxidant system was not described neither suspected.

Finally, lacking any specific intended action, the amounts of these substances to be assumed were reasonless high as compared to the approved Nutrient Reference Values (NRV): folic acid 800 microg (NRV=200 microg); vitamin B12 2.5 mg (NRV=2.5 microg).

The patent application U.S. Pat. No. 5,597,585 (Williams & Williams 1997) discloses the usefulness of an empirical nix of high doses of vitamins and substances based on the rationale that large amounts are better than physiologic ones. Such a concept, very questionable from a medical point of view and in contrast with the strict limits for human administration imposed by both the FDA in the USA and the EFSA in the EU, sustained the inclusion in the nutritional composition of Williams & Williams 1997 of a wide list of substances assembled without any specific rationale and in their supraphysiologic amounts. These high amount substances, among many others, included: folic acid 0.3-0-6 mg (NRV 0.2 mg); niacinamide 20-50 mg (NRV=16 mg); vitamin B2 30-250 mg (NRV=1.4 mg); vitamin B12 30-250 mg (NRV=2.5 microgr); vitamin B6 30-150 mg (NRV=1.4 mg); zinc 15-30 mg (NRV=10 mg) and; L-cysteine 660-1000 mg.

The patent application US 2002/182196 A1 (McCleary 2002) discloses a nutritional composition made of a wide list of substances, including folates. B vitamins and substances useful to the methylation balance, based on a holistic approach allowing to predict all that could have been potentially useful to the neurologic metabolism whatever the underlying problem.

The patent application US 2007/065456 A1 (Woods 2007) discloses a method to supplement human diet by the combined use of multiple nutritional compositions and intended to modulate inflammatory processes. The supplements to be used were based on herbal extracts of *Wasabia japonica* and/or *Syliburn marianum* and/or *Cynara scolimus*. The supplementation was in case to be completed with other substances including folic acid, niacin, zinc, betaine HCl and trimethylglycine. The inclusion of theses other substances in addition to the herbal extracts was just incidental as they had been separately included in the already existing nutritional formulae to be combined.

The method of supplementation should have been of benefit to humans suffering from acute or chronic inflammation resulting in the occurrence of several diseases including hearth diseases, Crohn disease and diabetes.

The patent US 2007/0116779 A1 (Mazzio 2007) discloses a nutritional composition for the treatment of Parkinson disease containing substances aimed at correcting the energy failure, the oxidation of catecholamines and the inflammation, which was basically achieved by administering substances favoring the anaerobic glycolysis. Other substances were to be optionally added to achieve ancillary actions with a positive effect on Parkinson disease. Based on the occurrence of high homocysteine levels in Parkinson disease Mazzio 2007 also mentioned ancillary substances intended to decrease homocysteine level within the brain, namely folic acid, betaine HCl, vitamin B6 and vitamin B12. This combination is indeed effective in lowering plasma homocysteine, but Mazzio 2007 did not consider that folic acid and vitamin 1312 do not pass the blood brain barrier and the proposed intervention was devoid of efficacy on Parkinson disease.

Definitions

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference; thus, the inclusion of such definitions herein should not be construed to represent a substantial difference over what is generally understood in the art.

Within the framework of the present description and in the subsequent claims, except where otherwise indicated, all numbers expressing amounts, quantities, percentages, and so forth, are to be understood as being preceded in all instances by the term "about". Also, all ranges of numerical entities include all the possible combinations of the maximum and minimum numerical values and all the possible intermediate ranges therein, in addition to those specifically indicated hereafter.

The term "active form" herein refers to the metabolite form of the inactive prodrug that is metabolized within the body into its active form.

The term "Pharmaceutically acceptable salts or derivatives" herein refers to those salts or derivatives which possess the biological effectiveness and properties of the salified or derivatized compound and which do not produce adverse reactions when administered to a mammal, preferably a human. The pharmaceutically acceptable salts may be inorganic or organic salts; examples of pharmaceutically acceptable salts include but are not limited to: carbonate, hydrochloride, hydrobromide, sulphate, hydrogen sulphate, citrate, maleate, fumarate, trifluoroacetate, 2-naphthalenesulphonate, and para-toluenesulphonate. Further information on pharmaceutically acceptable salts can be found in Handbook of pharmaceutical salts, P. Stahl, C. Wermuth, WILEY-VCH, 127-133, 2008, herein incorporated by reference. The pharmaceutically acceptable derivatives include the esters, the ethers and the N-oxides.

The term "physiologically acceptable excipient" herein refers to a substance devoid of any pharmacological effect of its own and which does not produce adverse reactions when administered to a mammal, preferably a human. Physiologically acceptable excipients are well known in the art and are disclosed, for instance in the Handbook of Pharmaceutical Excipients, sixth edition 2009, herein incorporated by reference.

The terms "comprising", "having", "including" and "containing" are to be construed as open-ended terms (i.e. meaning "including, but not limited to") and are to be considered as providing support also for terms as "consist essentially of", "consisting essentially of", "consist of" or "consisting of".

The terms "consist essentially of", "consisting essentially of" are to be construed as a semi-closed terms, meaning that no other ingredients which materially affects the basic and novel characteristics of the invention are included (optional excipients may thus be included).

The terms "consists of", "consisting of" are to be construed as a closed term. The term "vitamin B6" herein refers to a group of vitamers including pyridoxine, pyridoxamine, pyridoxamine 5'-phosphate; pyridoxal 5'-phosphate and the pharmaceutically acceptable salts or derivatives thereof, The term "betaine" herein refers to glycine Maine, i.e. N,N,N-trimethylglycine and the pharmaceutically acceptable salts or derivatives thereof.

The terms "antioxidant" and "direct antioxidant" refers to substances exerting an intrinsic antioxidant power, i.e. substances that are able in vitro to reduce (i.e. release electrons to) other substances.

The term "essentially free of antioxidants" is to be considered as a semi-closed term, meaning that no "antioxidants" has been intended to be added to the composition. The total amount of antioxidants as a result of unintended contamination is therefore well below 0.05%, preferably below 0.01%. Most preferred is a composition in which no amount of any antioxidant can be detected with standard analytical methods used in pharmaceutical technology.

Within the framework of the present description and in the subsequent claims, the term "Delayed Neurological Development Syndromes" is used to indicate all of the following listed neurological diseases including: ADD—Attention Deficit Disorder, ADHD—Attention Deficit Hyperactive Disorder, Dyslexia, Dyspraxia, Dyscalculia, Dysgraphia, Dystonia, PDD—Pervasive Developmental Disorder, DAMP—Deficits in Attention, Motor control and Perception.

The term "pediatric population" herein refers to that part of the population from birth to eighteen years.

DETAILED DESCRIPTION OF THE INVENTION

The inventor has observed that dietary supplementations of antioxidants and/or folic acid have a limited clinical benefit in improving the oxy-redox balance and in preventing newborn defects and exposure to higher doses may even cause pathologic consequences (i.e. reductive stress).

The present invention relates to pharmaceutical, dietary and/or food compositions, preferably dietary supplements, exerting indirect antioxidant activity, i.e. stimulating and feeding the endogenous antioxidant system, aimed at achieving an effective oxy-redox homeostasis together with healthy processes of cell growth and differentiation, including DNA methylation and genomic profiling, without incurring in any reductive stress as observed when direct antioxidants are used.

In physiologic conditions any excess of reactive oxygen species (ROS) and of reactive nitrogen species (RNS) activates removal by means of a variety of biochemical reactions and enzymes forming an anti-oxidant cascade that leverages on a wide list of mediators. These include enzymatic (superoxide dismutase-SOD, glutathione peroxidase-GPx, catalase-CAT) and non-enzymatic (ascorbic acid-vitamin C, tocopherol-vitamin E, carotenoids, flavonoids and others) antioxidants. On top of this cascade, there is a kind of redox buffering system based on a thiol antioxidant, the tripeptide glutathione (GSH) (Banerjee R. *Redox outside the box: linking extracellular redox remodeling with intracellular redox metabolism. J Biol Chem.* 2012; 287(7):4397-402). Besides acting as a cofactor for GPx, GSH can directly scavenge hydroxyl radicals and singlet oxygen. More importantly, GSH is able to regenerate the most important cellular antioxidants including vitamins C and E and the oxy-redox co-enzymes NAD and NADP. The synthesis of intracellular GSH is largely dependent on the so-called trans-sulfurations pathway having as the starting substrate homocysteine that is trans-sulfurated to cystathionine by the enzyme cystathionine beta synthase (CBS) and thereafter forms cysteine. Cysteine is then complexed with glutamic acid and glycine to form the tri-peptide GSH. The pathway is regulated at its first step as the CBS enzyme is redox-regulated, i.e. it transits into its active form after spontaneous oxidation that occurs proportionally to the oxidative load. The activated CBS will however acquire high activity only after each of the 4 enzyme subunits will bind a molecule of S-adenosylmethionine (SAMe) exerting an allosteric up-regulation Ereño-Orbea J et al. *Structural insight into the molecular mechanism of allosteric activation of human cystathionine β-synthase by Sadenosylmethionine. Proc Natl Acad Sci USA.* 2014; 111(37):E3845-52). SAMe is itself the end-product of homocysteine re-cycling by re-methylation within the one carbon cycle (1CC). Thus, the antioxidant cascade will receive adequate feed of reducing equivalents in the form of GSH only if the 1CC will be efficiently cycling.

The 1CC is the pathway producing activated methyl groups in the form of 5-adenosyl-methionine (SAMe) for the transmethylation reactions, including DNA methylation for epigenetic signaling. Briefly, the methyl group of methionine is activated by adenylation to SAMe that, after releasing the methyl groups, forms S-adenosyl-homocysteine and thereafter homocysteine. Homocysteine, besides being a precursor of GSH, can be re-methylated to methionine by: a) a methyl group provided by betaine (trimethylglycine); or, by a methyl group passing from methyl-tetrahydrofolate to cobalamin to form methyl-cobalamin and finally to homocysteine. To do so homocysteine gets coordinated to an enzyme-bound zinc (zinc finger) to form a reactive thiolate. The enzyme of concern is Methionine Synthase or Methionine Transferase (MTR). MTR is primed into a reactive state by the transfer of a methyl group from methyl-tetrahydrofolate to an enzyme-bound cobalamin to form methylcobalamin. Such transfer necessitates another enzyme, Methionine Transferase Reductase (MTRR). The primed methyl group is finally released to homocysteine that is re-cycled to methionine.

It has been now understood that, while the 1CC upregulates GSH synthesis, the activity of the 1CC is in turn dependent on GSH availability. It has been indeed noted that several of the main and regulating enzymes within the 1CC are oxy-reductases that are known to depend for their activity on the availability of the reduced form of the oxy-redox co-enzymes NAD and/or NADP (i.e. NADH and NADPH). These enzymes include: DiHydroFolate Reductase (DHFR) and Methyl-TetraHydroFolate Reductase (MTHFR), both responsible for the reductive activation of dietary folates, i.e. for the availability of methyl-tetrahydrofolate; Methionine Transferase Reductase (MTRR), responsible for the reductive activation of MTR-bound vitamin B12 to methylcobalamine, and; Choline DeHydrogenase (CHDH), responsible for the conversion of choline to betaine. NAD/NADP are recycled to their reduced form from GSH. Thus, The balance of NAD/NADP in their oxy or redox form and the performance of oxy-redox enzymes is directly dependent on intracellular GSH availability. The consequence is that there will not be activated methyls (from both methyltetrahydrofolate and betaine) for the re-methylation of homocysteine if the output of GSH is low.

The present invention is based on this new understanding of oxy-redox homeostasis. Indeed, the cross-regulation between the two pathways, transmethylations and transulfurations, configures a dynamic balance creating equilibrium between the two so that homocysteine may be preferentially funneled into re-methylation to methionine or into transulfuration to GSH according to the need. Any oxidative load that exceeds the buffering capacity of the system and/or absolute or relative dietary shortages of the key micronutrients will generate a vicious circle: 1) the lack of SAMe will decrease the activation of CBS with less of GSH produced; on the other side, 2) the lack of GSH reflects in a shortage of NAD/NADP in their reduced form resulting in low activity of the dehydrogenases responsible for providing methylfolate, methylcobalamin and betaine for homocysteine re-methylation and SAMe availability. The final outcome is a down-regulation of the activity of both pathways while homocysteine levels start to grow. Once this double blockade is in place both the physiologic antioxidant system and the transmethylations ensuring the epigenetic signaling undergo progressive deterioration because the usual sources of methyl donors (dietary folates and Maine from endogenous choline metabolism) are not anymore effective.

It has been now surprisingly discovered that the above vicious circle can be interrupted for a fast resumption of the cell antioxidant capacity and of the epigenetic processes by supplementing the diet with already activated methyl donors, namely methylfolate, methyl-cobalamin and betaine, provided at very physiological amounts. The availability of some preformed methylcobalamine will indeed allow some activity of MTR for an initial homocysteine re-methylation even if the activating enzyme MTRR is still under oxidative blockade. As well, some amounts of methylfolate will allow the unblocked MTR to process some homocysteine even if the folate activating enzymes DHFR and MTHFR are still under oxidative blockade. Finally, betaine will feed the BHMT reaction even though its availability from choline had been hampered by the oxidative blockade of CHDH. Some bioavailable zinc (i.e. chelated form) is also to be provided: zinc does not leverage on body reservoirs and depends on daily assumption and it is necessary to bind homocysteine to the enzymes zinc fingers. It is to be noted that, besides MTR, also the other two enzymes responsible for homocysteine processing, CBS and BHMT, work by means of zinc fingers. Once the initial blockade is removed by this combined support of activated substrates and some GSH starts to be available, the cell became again able to process also the dietary sources of folates and the endogenous sources of choline. Some physiologic amounts of riboflavin and niacin, essential co-factors of MTHFR, will now be useful to aid MTHFR to activate dietary folates whereas physiologic amounts of vitamin B6, essential co-factor for CBS, will ensure full efficiency of tansulfurations for high GSH output. The final effect is a virtuous circle lifting antioxidant defenses and DNA methylation up to the current need for a full efficiency of the cell. The homeostatic regulation will regulate the process according to the cell need with no risk to create any reductive stress as seen with the administration of direct antioxidants.

The supplementation of bioavailable SH groups, i.e. cysteines, will also be useful to feed GSH synthesis downstream to the CBS reaction so to allow an expansion of the global GSH and GSSG (oxidized form) pool, if it is needed. Cysteine is not soluble and cannot be absorbed by oral administration, thus it cannot be used as a dietary supplement. N-acetyl cysteine is a good source of bioavailable cysteine after oral administration, but it is not allowed for use as a dietary supplement in several countries. Indeed, the natural dietary sources of SH groups are cysteines of sulphurated proteins. Here cysteine is complexed with other cysteine within the protein by means of a di-sulphur bridge: when the protein is digested into the gut the two cysteines forming each di-sulphur bridge are released as a soluble and absorbable dimer (Cysteine-S-Cysteine) called cystine. Once into the cells, cystine dissociates back into two cysteines that can be used within metabolic reactions. The resolution of the di-sulphur bridge of cystine consumes reducing power, hence cystine has never been used as part of antioxidant supplementations. It has been now surprisingly discovered that cystine is very efficient in expanding the GSH pool if provided together with the ready substrates above mentioned. Indeed, once the other substances (methylfolate, methylcobalamin, betain, zinc) remove the initial blockade to GSH production, some GSH becomes available to open the cystine di-sulphur bridge resulting in 2 cysteines and 2 GSH potentially produced from one GSH consumed.

The timed availability (synthesis) of GSH also benefits the cell energetic balance. The energy substrates are processed into mitochondria by the Krebs cycle that stores the released energy in the form of NADH. The reducing equivalents of NADH are then used to reduce molecular oxygen within the respiratory chain and the released energy is used to produce ATP. The reduction of molecular oxygen to water is a two-step process having the hydroxyl radical OH' as the intermediate product. The second step of the reaction has a lower yield so that in standard conditions about 3% of the processed oxygen is lost as hydroxyl radical (hydroxyls leakage). When the pace of energy production increases, typically occurring in high energy demand cells as motoneurons, developing gametes and embryos and muscles during exercise, the rate of hydroxyls leakage increase significantly. This is the main source of endogenous oxidative load. Aiming to avoid massive damages leading to mitochondrial permeability transition and cell apoptosis several compensating mechanisms are in place: I) part of the hydroxyl radicals are scavenged by GSH by the GPx reaction; 2) the stations of the respiratory chain get reversibly inhibited by means of a series of reactions where the main one is glutathionilation, i.e. direct binding of GSH to the respiratory enzymes; 3) Hydroxyl radicals get dismutated to hydrogen peroxide ($H_2O_2$) that diffuses to the plasma membrane to oxidate the epimerase enzyme linked to the insulin receptor so to inhibit the activation of the insulin receptor and to create an insulin resistance that avoids further energetic substrates to enter the cell. Thus, when oxidative stress, i.e. low GSH generation, occur the energy production is down-regulated to avoid final mitochondrial damage. Low energy supply to demanding cells and insulin resistance possibly evolving to a disturbed glucose metabolism are the bill paid.

It has been now surprisingly discovered that the dietary supplementation with already activated methyl donors, namely methylfolate, methyl-cobalamin and betaine, and with the other co-factors, such as riboflavin, niacin, vitamin B6, L-cystine and zinc, provided at very physiological amounts, is able to induce a fast recovery and/or upregulation of mithocondrial energy output which results in avoidance of damages to high energy demanding cells, in the removal of insulin resistance, if any, in the improvement of the glucose uptake and metabolism and in enhanced ability to sustain intensive physical activity.

In summary, the inventor has surprisingly found that the supplementation of the composition according to the invention does actually provide an enhancement of the antioxidant defenses whose magnitude is larger than that achievable by the administration of direct antioxidants and that is devoid of any risk of imbalance toward a reductive stress because subject to the regulation of the natural cellular homeostasis. Besides up-regulating the physiologic antioxidant defenses, the supplementation of concern will also favor DNA methylation and epigenetics and will up-regulate the energy production.

According to a preferred embodiment of the present invention a combination of methylfolate, methylcobalamin, chelated zinc, betaine (trimethylglycine), riboflavin, niacin and L-cystine at physiologic amounts is used to up-regulate and/or to re-activate the endogenous antioxidant system and the DNA methylation in subjects known or suspected to suffer from oxidative stress.

According to another preferred embodiment of the present invention a combination of methylfolate, methylcobalamin, chelated zinc, betaine (trimethylglycine), riboflavin, niacin and L-cystine at physiologic amounts is used to up-regulate and/or to restore the energy production within mitochondria, to remove insulin resistance and to improve glucose metabolism.

According to a first aspect thereof, the present invention relates to a composition comprising:

a) methyl-tetra-hydrofolate and/or a pharmaceutically acceptable salt thereof in an amount comprised between 100 and 800 µg of folic acid equivalents, preferably 150 to 600 µg, more preferably 200 to 400 µg;

b) methylcobalamin and/or the pharmaceutically acceptable salts thereof in an amount comprised between 0.5 and 10 µg, preferably 1.5 to 5 µg, more preferably 2 to 3 µg of cyanocobalamin equivalents;

c) at least two vitamins B selected among vitamin B2, nicotinamide, vitamin B3 and vitamin B6 and/or the pharmaceutically acceptable salts or derivatives thereof in an amount comprised between 0.4 µg and 40 mg, preferably 1.5 µg to 32 mg, more preferably 2 µg to 18 mg;

d) a betaine and/or the pharmaceutically acceptable salts or derivatives thereof, preferably trimethylglycine hydrochloride, in an amount comprised between 100 and 2000 mg, preferably 150 to 1000 mg, more preferably 200 to 400 mg;

e) a chelated zinc compound in an amount comprised between 5 and 50 mg, preferably 6 to 20 mg, more preferably 8 to 12 mg of zinc equivalents;

f) a cysteine derivative in an amount comprised between 100 and 2000 mg, preferably 150 to 1000, more preferably 200 to 400 mg.

Advantageously, methyl-tetra-hydrofolate provides a source of metabolically active methyl groups for the reaction of methionine transferase (MTR) also in case of oxidative inactivation of MTHFR.

Advantageously, methylcobalamin allows to support the transfer of the active methyl group to homocysteine also in case of oxidative inactivation of MTRR.

Both folates and vitamin B12 in their activated forms, respectively methyl-tetra-hydrofolate and methylcobalamin, are the only soluble and physiologically circulating forms of such vitamins as well as the forms passing the blood brain barrier.

Advantageously, betaine allows to provide substrates to the BHMT reaction for homocysteine re-methylation also in case of reduced betaine synthesis due to the oxidative blockade of CHDH.

Advantageously, the chelated zinc compound acts as co-factor for several key enzymes working by means of zinc fingers such as MTR, BHMT and CBS to whom it is necessary to bind the homocysteine substrate.

According to another preferred embodiment, the chelated zinc compound is selected from the group comprising zinc amino acid chelate, zinc arginate, zinc ascorbate, zinc aspartate, zinc bisglycinate, zinc caprylate, zinc cysteinate, zinc ethanolamine phosphate, zinc fumarate, zinc glutamate, zinc glycinate, zinc histidinate, zinc ketoglutarate, zinc lysinate, zinc malate, zinc methionate, zinc orotate, zinc picolinate, zinc pidolate, zinc proteinate, zinc succinate, zinc tartrate, zinc taurate and zinc undecyclinate.

It is to be noted that zinc, although being an essential nutrient necessary to many physiologic activities, is not an antioxidant, i.e. it is not able to directly reduce any other substances.

Preferably, the cysteine derivative is L-cystine.

Advantageously, L-cystine acts as the cysteine donor aimed at sustaining the synthesis of GSH downstream to the CBS reaction so to further increase the output of GSH and to enlarge the cycling pool of reduced and oxidised glutathione. N-acethyl cysteine is an as well suitable cysteine donor.

According to a preferred embodiment of the present invention, vitamin 93 or nicotinamide is present in an amount comprised between 4 and 40 mg, preferably 8 to 32 mg, more preferably 12 to 18 mg. Advantageously, vitamin B3 (niacin) and/or nicotinamide allow to support the activation of dietary folic acid by means of the reaction of the MTHFR.

According to a preferred embodiment of the present invention, vitamin B2 or riboflavin is present in an amount comprised between 0.4 and 5 mg, preferably 1 to 2 mg per day, more preferably 1.2 to 1.6 mg. Advantageously, vitamin B2 (riboflavin) acts as further support to the reaction of MTHFR.

According to a preferred embodiment of the present invention, vitamin B6 is present in an amount comprised between 0.4 and 5 mg, preferably 1 to 2 mg, more preferably 1.2 to 1.6 mg.

Preferably, vitamin B6 is as pyridoxine or pyridoxine hydrochloride.

Advantageously, vitamin B6 acts as a necessary cofactor for the CBS.

In a preferred embodiment of the invention, the composition comprises:

a') L-5-methyltetrahydrofolate in an amount comprised between 100 and 800 µg of folic acid equivalents, preferably 150 to 600 µg, more preferably 200 to 400 µg;

b'$_1$) vitamin B3 or nicotinamide in an amount comprised between 4 and 40 mg, preferably 8 to 32 mg, more preferably 12 to 18 mg;

b'$_2$) vitamin B2 in an amount comprised between 0.4 and 5 mg, preferably 1 to 2 mg per day, more preferably 1.2 to 1.6 mg;

b'$_3$) methylcobalamin in an amount comprised between 0.5 and 10 µg, preferably 1.5 to 5 µg, more preferably 2 to 3 µg of cyanocobalamin equivalents;

b'$_4$) pyridoxine or pyridoxine hydrochloride in an amount comprised between 0.4 and 5 mg, preferably 1 to 2 mg, more preferably 1.2 to 1.6 mg;

c') trimethylglycine or trimethylglycine hydrochloride in an amount comprised between 100 and 2000 mg, preferably 150 to 1000 mg, more preferably 200 to 400 mg;

d') zinc bisglycinate in an amount comprised between 5 and 50 mg, preferably 6 to 20 mg, more preferably 8 to 12 mg of zinc equivalents;

e') L-cystine in an amount comprised between 100 and 2000 mg, preferably 150 to 1000, more preferably 200 to 400 mg.

In a preferred embodiment of the present invention, the composition is essentially free of antioxidants.

In a preferred embodiment of the present invention the compositions are to be assumed on a daily basis by any systemic route, including but not limited to oral, injective and trans-rectal. The pharmaceutical, dietary and/or food compositions of the present invention are preferably formulated in solid or liquid form. Said solid form being selected from tablet, capsule, granule, or suppository, more preferably tablet, Said liquid form being selected from soluble granule, drinkable solution or injection.

In a preferred embodiment of the invention, the composition according to the invention further comprises at least one physiologically acceptable excipient.

To obtain the pharmaceutical, dietary and/or food compositions according to the present invention the following classes of known excipients are preferably used: anti-caking agents (mono and di-glycerides of fatty acids), stabilizers (cross-linked carboxymethyl cellulose), bulking agents (microcrystalline cellulose), sweeteners, surfactants (cationic, anionic or non-ionic), diluents, aggregating agents or binders, lubricants, glidants, solubilizers, emulsifiers, humectants, flavoring agents, coating agents, colorants, acidity regulators, or a mixture thereof. Preferably, bulking agents, anticaking agents, stabilizers and a mixture thereof.

According to a second aspect thereof, the present invention relates to the aforementioned compositions for use as medicament.

Advantageously, the compositions according to the invention administered to subjects known or suspected to suffer from oxidative stress allow to achieve effective oxy-redox homeostasis, efficient epigenetics and up-regulated energy production without the use of direct antioxidants and without incurring in reductive stress resulting from direct antioxidants.

The susceptibility to oxidative stress and methylation imbalance also depends on the individual genetic substrates. The most common genetic variant of concern is the polymorphism of the enzyme 5,10-MethyleneTetraHydroFolate Reductase (MTHFR), which catalyzes the reduction of 5,10-methylene-tetrahydrofolate to 5-methyltetrahydrofolate, the methyl donor for the conversion of homocysteine to methionine and for the synthesis of purines, DNA, and RNA. Two polymorphisms are responsible for reduced activity of the MTHFR enzyme: the C677T variant, with an alanine to valine exchange and the A1298C variant, leading to glutamate-alanine substitution. These genetic variants of MTHFR associate with reduced enzymatic activity that can be as low as 25% in 677TT homozygous and 48% in the combined 677CT and 1298 AC heterozygous (van der Put N. M. J. et al.: *A Second Common Mutation in the Methylenetetrahydrofolate Reductase Gene: An Additional Risk Factor for Neural-Tube Defects, Am. J. Hum. Genet.* 1998; 62:1044-1051).

The frequency of these pathologic MTHFR variants is very high although variable according the population of concern with a north to south gradient for increasing prevalence of the pathologic variants. In example, in a series of newborns from southern Italy (Zappacosta B. et al,: *Genotype Prevalence and Allele Frequencies of* 5,10-*Methylenetetrahydrofolate Reductase (MTHFR) C677T and A1298C Polymorphisms in Italian Newborns. LABMEDICINE*, Volume 40 Number 12, December 2009) the frequency of the 677T MTHFR variant was 51% for the heterozygous and 25% the homozygous detect whereas the 1298C variant was carried by respectively 12.5% (homozygous) and 40.5% (heterozygous). These frequencies were lower, respectively 41% and 15% for 6771 hetero and homozygous, when tested in a northern USA population of oncologic patients (Robien K. et al.: *Methylenetratrahydrofolate Reductase Genotype Affects Risk of Relapse alter Hematopoitic Cell Transplantation for Chronic Myelogenous Leukemia. Clin. Cancer Res* 2004; 10: 7592-7598). However, the latter study did not find any subject carrying an association of either 677TT or 1298CC homozygous with the heterozygous state of the other variant likely indicating that such association would be lethal. Carriers of the 677T variant of the MTHFR are supposed to be at increased risk for a series of conditions including cardiovascular disease, neuro-degeneration, neural tube defects and autism. However, the best evident association of this defect is with male and female infertility.

Subjects carrying a heterozygous defective MTHFR variant may have high homocysteine levels that may be difficult to normalise. Subjects carrying any of the two mentioned variants with a homozygous state almost always exert very high homocysteine levels, sometime high enough to configure a high risk for thromboembolic events that requires an urgent treatment. In carriers of homozygous defective MTHFR variants the reduction of homocysteine level is commonly achieved by the administration of huge doses of folic acid, e.g. 5 mg that is 20 times its daily requirements. The large excess of substrate is supposed to compensate the reduced enzymatic activity, indeed this treatment is able to reduce homocysteine in most of the affected subjects. However, intensive supplementation of folic acid to carriers of the MTHFR defective variants can lead to the UnMetabolized Folic Acid (UMFA) syndrome. UMFA is associated with a reduction of natural killer cytotoxicity and defective capacity to remove malignant or pre-malignant cells (Ulric C. M and Potter J. D.: *Folate Supplementation: Too Much of a Good Thing? Cancer Epidemiol Biomarkers Prev* 2006; 15: 189-193). Thus, the possibility to reduce circulating homocysteine in these subjects without exposing them to the consequences of excessive unmetabolised folic acid has a relevant clinical value.

Advantageously, the compositions according to the invention allow to obtain the reduction of the circulating homocysteine both in subjects carrying the wild type gene of MTHFR and in subjects carrying a defective gene variant of the same enzyme. This is achieved by administering normal doses of folates (e.g. 400 µg) if given, according to the present invention, in the form of methylthlate and together with the other above mentioned essential co-factors.

In addition, it has been now understood that the MTHFR variants are only one of the genetic issues affecting the 1CC and the antioxidant defenses and similar considerations applies also to other key enzymes of the pathway.

The MTR catalyzes the methylation of Homocysteine to generate methionine. The P1173L mutation, which results in replacement of proline by leucine at position 1173 of the amino acid sequence, causes megaloblastic anaemia and developmental delay by the age of year 2; however, a series of other mutations causing only a decreased activity of the enzyme due to shorter half-life have also been described (Watkins D et al. *Hyperhomocysteinemia due to methionine synthase deficiency, cblG: structure of the MTR gene, genotype diversity, and recognition of a common mutation, P1173L. Am J Hum Genet.* 2002; 71: 143-53).

Among these, the A2756G mutation, that is known to cause hyperhomocysteinemia, may circulate with high frequency: among an unselected groups of 125 Turkish children the AG heterozygous state had an incidence of 38% and 5% of them were GG homozygous (Aşlar L), Hakki T. *Prevalence of MTHFR, MTR and MTRR gene polymorphisms in Turkish patients with nonsyndromic cleft lip and palate. Gene Ther Mol Biol.* 2014; 16: 115-29).

The enzyme MTRR is responsible of the reductive activation of MTR, Deficient MTRR activity causes hyperhomocysteinemia and all symptoms of B12 shortage even in presence of normal B12 levels. The defective MTRR variant A66G has been clinically linked with high Homocysteine and occurs with a frequency almost as high as MTHFR variants: according to a very large survey study in the USA almost half of the USA population was heterozygous for MTRR A66G with the highest prevalence in the non-Hispanic white ethnic group (Yang Q-E et al. *Prevalence and effects of gene-gene and gene nutrient interactions on serum folate and serum total homocysteine concentrations in the United States: findings from the third NationalHealth and Nutrition Examination Survey DNA Bank. Am J Clin Nutr.* 2008; 88: 232-46).

The enzyme BHMT is responsible of homocysteine methylation using betaine (trimethylglycine) as the methyl donor. A long list of single nucleotide polymorphisms (SNPs) has been described, all of them implicated with the occurrence of reproductive, neoplastic and degenerative diseases, but always within variable associations with other SNPs of the same gene or of other genes of metabolic enzymes configuring a kind of genetic puzzle. In example, the G742A mutation was associated with the occurrence of any neural tube detect (NTD) in a USA population but only in the subgroup of mothers supplemented with folic acid whereas in non-supplemented mothers it had no influence (Boyles A L et al. *Neural tube defects and folate pathway genes: family-based association tests of gene-gene and gene-environment interactions. Environ. Health Persp.* 2006; 114(10): 1547-52), suggesting that a BHMT defect may be relevant only in conditions of folate shortage.

The enzyme CHDH, responsible to provide the betaine substrate to BHMT, may commonly occur with the G233T mutation that was proven to cause motility, structure and energy deficits in sperms of transgenic mice (Johnson A R et al. *Deletion of marine choline dehydrogenase results in diminished sperm motility. FASEB J.* 2010; 24(8): 2752-61).

As many as 150 clinically relevant mutations of CBS, the key enzyme for oxy-redox homeostasis, have been described. In most of the cases, they are non-sense mutations and also multiple alternatively spliced transcript variants may occur. The homozygous state for several of these genes is responsible for homocystinuria, a disease leading to death within the age of 20-30 years. The most common of these mutations, a substitution of threonine for isoleucine at codon 278 (I278T), was found to occur in heterozygous form in 11.7% of a control population (Tsai M Y et al. *High prevalence of a mutation in the cystathionine B-synthase gene. Am J Hum Genet.* 1996; 59:1262-7). It can lead to full homocystinuria or complete compensation according to the homo- or heterozygous state and to the combination with other genetic and protein splice variants but is usually associated with mild disease and may account for many subclinical disturbances of the 1CC and of homocysteine homeostasis.

In summary, MTHFR variants are only the tip of the iceberg because many other mutations, all of them occurring with a high frequency, may affect the same pathway and may be as well responsible for high homocysteine level and for increased susceptibility to the oxidative damages. Due to their high frequency, the occurrence of multiple enzymatic variants of the 1CC is a common finding. It can be postulated that many patients with MTHFR defective variants whose homocysteinemia is resistant to high doses of folic acid are indeed carriers of multiple genetic defects and that they would not benefit by an isolate folate supplementation, even if given as methylfolate. Genetic testing is of little help because we do not currently know all the possible variants involved and how many SNPs should be tested for each of them. The inventor has now understood that putting remedy to all of the currently known enzymatic polymorphisms of the 1CC is clinically possible and can be done independently of any genetic testing*. Advantageously, the compositions according to the invention allow to achieve effective oxy-redox homeostasis and homocysteine lowering independently of the occurrence of any of the above mentioned enzyme variants and of their possible combinations. Indeed, MTHFR variants have no negative influence if activated folates, i.e. methylfolate, is supplied. Similarly, the supply of methylcobalamine may overcome a possible MTR and/or MTRR defect. The deficit in CHDH activity can be compensated by supplementing ready betaine for the BHMT reaction. Finally, a supply with L-cystine may compensate most of the consequences of CBS mutations by providing cysteine for GSH synthesis downstream to the CBS reaction.

The daily ingestion of the composition according to the invention has the potential to improve both the deposition of DNA methylation marks and to restore the cellular antioxidant defenses and may be of help to conditions linked to the loss of genomic regulation developed during the adult life and the elderly. Indeed the DNA methylation marks may be removed during life, mainly due to environmental insults, and/or may be inactivated by means of oxidation of either the methyl-cytosine or the guanosine of CpG pairs within CpG islands. The loss of genomic: regulation will allow the extensive transcription of genes otherwise silenced or down-regulated leading to a chaotic phenotype responsible for tissue degeneration. This process is involved in neurodegenerative diseases affecting the central nervous system (e.g. Alzheimer disease, Parkinson disease, dementia) or the periferic nervous system (e.g. lateral amyotrophic sclerosis-ALS and multiple sclerosis-MS). In particular, this occurrence has been described as the mechanism leading to the development of Alzheimer disease in prospective primate models (Wu J. et al.: *Alzheimer's disease (AD) like pathology in aged monkeys following infantile exposure to environmental metal lead (Pb): Evidence for a developmental origin and environmental link for AD. J Neurosci.* 2008 January 2; 28(1): 3-9): the loss or inactivation of the methylation marks on the promoter of the gene coding for the pro-amiloid beta protein may cause excessive expression of said protein and its accumulation within the cerebral tissues followed by degeneration. This is further supported by the finding that Homocysteine levels are higher than controls in subjects with symptoms of Alzheimer disease and that Homocysteine levels correlate with the severity of the symptoms (Zheng Z. et al.: *Correlation between Behavioural and Psychological Symptoms of Alzheimer Type Dementia and Plasma Homocysteine Concentration. Biomed Res Int.* 2014; 2014:383494). A supportive intervention able to improve the efficiency of both DNA methylation and of antioxidant defenses has the potential to arrest or slow down the progression of the disease and, to some extent, to restore the signaling of the methylation marks on key genes.

In addition, neurodegenerations affecting the moto-neurons, e.g. ALS and Parkinson disease, are also pathogenetically linked to the so-called glutamate excito-toxicity that may be efficiently counteracted by the nutritional composition of the present invention (see thereafter in this document).

In a further aspect, the present invention relates to the use of the aforementioned compositions in the prevention and/or treatment of neurodegenerative diseases, preferably Alzheimer disease, Parkinson disease, dementia, Amyotrophic Lateral Sclerosis and Multiple Sclerosis.

Advantageously, the compositions according to the invention can be assumed daily by subjects carrying risk factors for developing neurodegenerative diseases to prevent or delay the clinical onset of said diseases.

The link between neurological development and the performance of the 1CC and of the antioxidant defences is well demonstrated by the protective effect of folic acid supplementation during pregnancy on the occurrence of neural tube defects (NTDs) and Autism Spectrum Disorders (ASDs). Similarly, metabolic imbalances affecting these pathways are also linked to the occurrence of other delayed neurological developments after birth. Besides ASDs, these syndromes include a variety of deficits that are named according to their main symptoms with a long list of names including: ADD—Attention Deficit Disorder, ADHD—Attention Deficit Hyperactive Disorder, Dyslexia, Dyspraxia, Dyscalculia, Dysgraphia, Dystonia, PDD—Pervasive Developmental Disorder, DAMP—Deficits in Attention, Motor control and Perception.

The Delayed Neurological Development Syndromes, with most of the available studies being focused on ASDs, have been clearly linked to disturbances of the 1CC metabolism and/or of the oxy-redox balance. Children with autism exert a metabolic profile consistent with impaired capacity for methylation (significantly lower ratio of SAMe to S-Adenosyl-Homocysteine) and increased oxidative stress (significantly lower ratio of reduced glutathione to oxidized glutathione) (James S. J et al.: *Metabolic biomarkers of increased oxidative stress and impaired methylation capacity in children with autism. Am J Clin Nutr* 2004; 80: 1611-7). Accordingly, dietary interventions aimed at improving either the folate status and the 1CC metabolism or the oxy-redox state by means of direct antioxidants resulted in marked improvements in clinical status (Frye R. E. & Rossignol D. A.: *Treatments for biomedical abnormalities associated with autism spectrum disorder. Frontiers in Pediatrics* 2014; Volume 2: Article 66). However no treatments able to positively modulate at the same time both the 1CC metabolism and the oxy-redox state have been available for testing so far. Moreover, the only folate and cobalamin forms that circulate to the brain are their reduced forms, methyl-folate and methy-cobalamin, Thus, former dietary interventions delivering plain folic acid have been likely ineffective in the high rate of ASDs children bearing a defective genetic variant of the enzymes MTHFR, MTR and MTRR.

In a further aspect, the present invention relates to the use of the aforementioned compositions in the prevention and/or treatment and/or delay the progression of Autism Spectrum Disorders (ASDs) or Delayed Neurological Development Syndromes, preferably in pediatric population.

According to a further aspect, the present invention relates to the use of the aforementioned compositions as pregnancy support and/or as perinatal support.

In a preferred embodiment, the compositions according to the invention are used as a pregnancy support to mothers (preferably in the first trimester) or as a perinatal support (preferably 3 months before conception) to both the parents.

Advantageously, said treatment can prevent the occurrence of newborn defects, including neural tube defects and autism spectrum disorders.

According to another aspect, the present invention relates to the use of the aforementioned compositions as fertility enhancer. Gametes and embryos development and maturation is indeed a high energy demanding process and the up-regulation of the energy balance obtained with the present nutritional comnination may significantly contribute. Timed availability of high cellular energy is essential to gametes to complete their meiotic division, in particular to assembly the meiotic machinery and to achieve fast and complete migration of the chromosomes in the parental cells. Hence, a higher energy supply might recude the incidence of aneuploidies in both the sperms and the oocytes. High energy is also required for embryo activation, growth and differentiation. In particular, high energy is required for the closure of the embryonic spinal cord and any shortage may further increase the risk for neural tube defects in the newborns.

Advantageously, the compositions according to the invention can improve the fertility potential in both or either partners of couples seeking parenthood either by natural conception or within Assisted Reproductive Technologies cycles.

A large part of women suffering from infertility problems is affected by the Poly Cystic Ovary Syndrome (PCOS) that is characterized by a variable combination of ovarian cystic degeneration, insulin resistance and hyperandrogenism. Women with PCOS often experience anovulatory cycles due to early arrest of follicular development. Little doubt exist on the fact that PCOS is linked to oxidative stress and elevated homocysteine in plasma and follicular fluid is the best known marker. However, most of the imbalances occurring in PCOS are triggered by insulin resistance that will in turn cause an increase androgen synthesis from the adrenal gland and decrease hepatic release of steroid binding globulins resulting in an absolute or relative hyper-androgenism, which will be then interfering with the development of the ovarian follicules. As already explained in this document, insulin resistance is a compensatory mechanism intended to avoid further entrance in the cell of energy substrates when the mitochondria are already producing too much of ROS. Advantageously, the compositions according to the invention can improve the energy production from mitochondria so that energy substrates became processable, which results in the removal of insulin resistance and in the regression of most of the signs and symptoms of PCOS, including the fertility problems.

In a preferred embodiment, the compositions according to the invention can be used in the treatment of PCOS with the aim to improve the symptoms and the metabolic balance and to restore ovulation and fertility by means of an improved oxy-redox status, of an improved energy metabolism removing insulin resistance and of a decreased burden of circulating and follicular homocysteine.

The same positive effects of the compositions on insulin resistance may be of help in improving glucose tolerance in patients with type 2 diabetes mellitus (DM2) with a clear advantage over the existing pharmaceutical interventions. DM2 patients under insulin treatment are indeed predicted to suffer from the artificial uptake of glucose, induced by supra-physiological therapeutic insulin, that forces their mitochondria to process energy substrates that they were trying to keep outside by means of insulin resistance. Keeping this non physiologic glucose influx, the mitochondria undergo excess of ROS production up to final and definitive denaturation of the enzymes of the respiratory chain followed by mitochondrial permeability transition and death and by cell apoptosis. The inventor has now understood that this mechanism, besides contributing to tissue damages, is also a reason for the fast progression to insulin dependence of DM2 patients starting the insulin treatment, Indeed, the beta cells of the pancreas responsible for insulin release are their self sensitive to insulin. Thus therapeutic insulin will force the beta cells to incorporate energetic substrates triggering the final mitochondrial death and beta cells apoptosis, which leads to a fast onset of dependence from therapeutic insulin. The occurrence of this insulin toxicity in the clinical setting is strongly supported by the outcomes of the milestone ACCORD study (*ACCORD data and solely monitoring committee. Effects of Intensive Glucose Lowering in Type* 2 *Diabetes. N Engl J Med* 2008; 358: 2.545-59). The study included 10,251 DM2 patients with a median glycated hemoglobin level of 8.1%. Patients were randomly assigned to receive intensive therapy (targeting a glycated hemoglobin level below 6.0%) or standard therapy (targeting a level from 7.0 to 7.9%) based on the hypothesis that a more intensive glucose lowering treatment would have been of benefit to the long term outcomes. Opposite, the study was early withdrawn and published after 3.5 years of follow-up because the intensive therapy "recorded increased mortality and did not significantly reduce major cardiovascular events". It is clear that the above described mechanism of insulin toxicity to mitochondria may have played a main effect in this negative outcome.

DM2 patients treated with oral antidiabetic drugs, mainly metformin, are less exposed to the above described mitochondrial toxicity but in turn are known to suffer from a direct negative effect of metformin that increases circulating homocysteine. Metformin indeed associates/causes folate shortage and inhibits the activity of vitamin B12, The increased homocysteine is in turn known to cause a faster progression of diabetic peripheral neuropathy. It is also known that diabetic patients carrying a C677T mutation of the MTHFR gene, further weakening the 1CC metabolism, are at higher risk to develop diabetic peripheral neuropathy, including retinopathy, and the same may apply to those carrying other previously described genetic variants of the enzymes of the 1CC.

Advantageously, the compositions according to the invention can improve the glucose uptake and the insulin resistance in DM2 patients and thereby improve or correct the disease compensation. Further advantageously, this effect will be occurring in any subjects, independently of the individual genetic substrate including possible variants of the concerned enzymes.

In a preferred embodiment, the compositions according to the invention can be used in the treatment of type 2 diabetes mellitus with the aim to improve the glucose metabolism, to decrease or avoid the need for antidiabetic drugs and to reduce or delay the occurrence of diabetic peripheral neuropathy by means of an improved oxy-redox status, of an improved energy metabolism removing insulin resistance and of a decreased burden of circulating homocysteine. In another preferred embodiment the compositions according to the invention are used as an adjuvant to oral antidiabetic drugs, including metformin, to counteract the homocysteine increase caused by said drugs.

In a further aspect, the present invention relates to the use of the aforementioned compositions in the prevention and/or treatment of cardiovascular diseases and of hypertension whether or not associated to DM2.

Advantageously, the compositions according to the invention can decrease the circulating homocysteine in subjects at increased risk of onset or relapse of cardiovascular diseases and in subjects with essential hypertension.

In a further aspect, the present invention relates to the use of the aforementioned compositions in the prevention and/or treatment of menopausal vasomotor symptoms (VMS), namely hot flashes and night sweats. VMS are frequently perturbing the perimenopausal age and the early menopause and sometimes persist in the long term. Current treatments are mainly based on estro-progestins substitutive therapy, that is often refused by the patients due to the counter effects, or on phytoestrogens, that have only a partial and short lasting efficacy in a minority of the patients.

The inventor has now understood that the main mechanism inducing the VMS is the so-called glutamate excitotoxicity: glutamate is an excitory neurotransmitter that may exacerbate many otherwise physiologic neuronal responses. Glutamate levels are indeed increased in menopausal women. This increase is primarily triggered by the decreased levels of estrogens and progesterone. More important, according to the inventor, the drop of estrogens and progesterone exacerbate the oxidative stress within the brain with a sharp increase of intra-cerebral homocysteine. Homocysteine is known to inhibit the re-uptake of glutamate from the synaptic space and to directly stimulate the glutamate receptors. Hence, intracerebral hyperhomocysteinemia causes excess of glutamate and/or glutamate receptor stimulation. The pre optic nucleus of the central nervous system, responsible for co-ordinating the thermoregulation responses, is particularly sensitive to glutamate excess. Thus, normal stimula requiring slight increases of the body temperature, especially during the night sleep, will result in excessive responses triggering the hot flashes and the sweats.

Advantageously, the compositions according to the invention can decrease the intracerebral excess of homocysteine and thereby decrease the glutamate system hyperactivation. Indeed, methyl-folate and methyl-cobalamin provided in the nutritional composition are able to pass the blood brain barrier and to exert their effect on homocysteine in combination with the other provided micronutrients.

In a preferred embodiment, the compositions according to the invention can be used in the treatment of menopausal vasomotor symptoms with the aim to decrease or eliminate their occurrence while at the same time positively influencing the metabolic balance of menopausal women.

In a further aspect, the present invention relates to the use of the aforementioned compositions to treat patients affected by coeliac disease either in the acute phase and during remissions to prevent relapses. Coeliac disease is an inflammatory status affecting the small intestine as a consequence of an immune reaction against the gluten proteins. Accordingly, the acute symptoms of the disease usually respond to a gluten-free diet, although a real and full histological remission is rarely observed. The disease is known to associate to folate an B12 deficits and the related anemia is often the starting symptom, and to high homocysteine level. Hyperhomocysteinemia and folate/B12 deficiency do not always and/or completely revert with the gluten-free diet, A treatment with high doses of folic acid, vitamin B12 and vitamin B6 was shown to decrease the homocysteine levels but no effect on disease progression was recorded or suspected. The inventor has now understood that the coeliac disease imbalance in methylation balance and oxy-redox status may be further complicated by the gluten-free diet because it causes shortage of the sulfhydryl groups usually consumed as part of the gluten proteins. It has been now surprisingly discovered that a full supplementation to the concerned pathways is able, besides normalizing circulating homocysteine, to shorten the time to healing and to prolong the time to relapse and/or to decrease the incidence of relapses of coeliac disease.

Advantageously, the compositions according to the invention can be used to fasten the clinical response to the gluten-free diet in coeliac patients, to achieve full histological remission besides clinical remission and to prevent the occurrence of relapses.

In a further aspect, the present invention relates to the use of the aforementioned compositions to boost the energy balance and the performance of athletes and of other subjects undergoing intensive physical activity. The inventor has indeed understood that the mitochondrial antioxidant power, read GSH level, is the rate limiting factor of the amount of energy, read. ATP, that each mitochondrion is able to release. As already explained, when the amount of ROS generated during ATP production increase, the mitochondria implement corrective actions to down-regulate the ATP output and consequently the release of hydroxyl radicals. If mitochondria are duly repleted with GSH, e.g. by means of a tailored nutritional support, the threshold for hydroxyl radical toxicity within the mitochondria lifts up proportionally to the availability of GSH, This will translate in increased energetic output and in improved physical performances. In addition, agonist athletes are often assuming creatine supplements to boost their acute muscular response. Although an otherwise positive risk to benefit ratio, creatine may induce disturbances of the methylation metabolism and an increase of homocysteine.

Indeed, after ingestion creatine is activated to phosphocreatine within the muscles to provide immediately available energy sources. After consumption phosphocreatine generates creatinine that is excreted, thereby increasing the daily turnover of creatine. Creatine is synthesized in the liver that consumes two molecules of SAMe and releases two molecules of homocysteine for each molecule of creatine produced. This is a massive activity that accounts for about 60% of the endogenous homocysteine production. The homocysteine overproduction resulting from the use of creatine supplements may cause long term health problems as well as may limit the positive effects of creatine assumption on the sport performance.

Advantageously, the compositions according to the invention can improve the energy balance in athletes and in subjects undergoing intensive physical activity. Further advantageously; the compositions according to the present invention does not contain any substances with pharmacologic activity or included by any means within the doping, hence it can be assumed by any athletes without incurring in negative counter effects or in doping sanctions. Further advantageously, the compositions according to the present invention may counteract the negative effect of creatine supplements on homocysteine and on the oxy-redox balance thereby improving the safety and the efficacy of creatine supplementation.

In a preferred embodiment, the compositions according to the invention can be used as a support to athletes and to subjects undergoing intensive physical activity to boost their energy production and their performance and to improve the safety and the efficacy of a possible creatine supplementation.

In a further aspect, the present invention relates to the use of the aforementioned compositions to support the growth and maturation of ovarian oocytes/follicles, embryos and stem cells undergoing to in vitro culture. A main problem encountered with the in vitro culture of ovarian oocytes/follicles, embryos and stem cells is their epigenetic stability and their resistance to the oxidative damage indeed, differently from in vivo conditions, in vitro cultures do not enjoy the metabolic support of the whole organism (e.g. liver and kidney functions) and entirely rely for their metabolic needs on the substances included in the culture medium of concern. For a series of technical, biochemical and industrial reasons all of the available culture media do not adequately support the need for antioxidant defenses, DNA methylation and energy production causing incomplete or defective maturation in the case of oocytes/follicles and embryos and the so-called cell line instability in case of cultures of stem cells. It has been now surprisingly discovered that the composition of the present invention, duly formulated as a ready to use liquid medium at a concentration ranging from 1 in 100 ml to 1 in 2000 ml of the amounts equivalent to a recommended daily human oral dose, is effective in adjusting the oxy-redox balance, in normalizing the epigenetic processes and in boosting the energy output of ovarian oocytes/follicules, embryos and stem cells undergoing in vitro culture.

In a preferred embodiment, the compositions according to the invention can be formulated as a liquid medium used as an add on to any culture medium to improve the oxy-redox balance, the epigenetic processes and the energy output of ovarian oocytes/follicles, embryos and stem cells undergoing in vitro culture.

In a preferred embodiment, the compositions according to the invention can be administered to mammals, particularly to humans. Preferably, the compositions according to the invention can be administered to adults or a pediatric population.

The daily dose and the duration of the treatment vary according to the indication, the age, and the patient's clinical situation.

The following examples are intended to better understand the invention, without in any way limiting it.

EXAMPLES

Example 1

A tablet for oral administration was formulated by including the daily dose of all the targeted nutritional substances as follows: Betaine (trimethylglycine) 200 mg; L-Cystine 200 mg; Zinc bis-glycinate equivalent to zinc 10 mg; Niacin 16 mg; Pyridoxine 1.4 mg; Riboflavin 1.4 mg; (6S)-5-methyltetrahydrofolic acid as glucosamine salt equivalent to folic acid 400 µg; Methylcobalamin in amounts equivalent to cyanocobalainin 2.5 µg. The excipients included microcrystalline cellulose, mono and di-glycerides of fatty acids, cross-linked carboxymethyl cellulose, stearic acid and silicon dioxide.

The resulting tablet had a global mass of 1300 mg and was of whitish colour, odourless and tasteless. The stability of the tablet was investigated under standard (25° C.±2° C.; 60% R.H.±5%) conditions up to 36 months and under accelerated conditions (40° C.±2° C.; 75% R.H.±5%) up to 9 months. The stability was assessed by monitoring the organoleptic properties, by checking the microbial load and by titration of the nutritional substances. All the results were within the approved range up to the end of the stability program in both the tested conditions.

Example 2

Ten male subjects regularly smoking 15 cigarettes per day or more assumed the composition formulated according to EXAMPLE 1, 1 tablet per day during 1 week or 1000 mg daily of vitamin C by the oral route for 1 week according to a cross-over design with a 1 month wash-out interval between the treatments. The plasma total antioxidant capacity (TAC) was measured by means of a colorimetric assay kit before and after each of the treatment periods in all subjects. The average TAC values expressed as µmol trolox equivalents increased from 472±36 to 522±32 (increase=11%) following one week supplementation with the powerful direct antioxidant vitamin C and from 468±31 to 565±36 (increase=21%) following one week supplementation with the composition according to the invention. Thus, the TAC increase provided by the aforementioned composition was of the same magnitude, if not higher, than that induced by full doses of a potent direct antioxidant.

Advantageously, in subjects chronically exposed to oxidative aggression, resulting in decreased total antioxidant capacity, the regular assumption of the composition according to the invention may help to restore adequate antioxidant capabilities.

Example 3

Ten young male subjects aged 18-25, following a healthy diet and virtually free from diseases assumed the composition formulated according to EXAMPLE 1, 1 tablet per day, for 1 week or 1000 mg daily of vitamin C by the oral route for 1 week according to a cross-over design with a 1 month wash-out interval between the treatments. The plasma total antioxidant capacity (TAC) was measured by means of a colorimetric assay kit before and after each of the treatment periods in all subjects. The average TAC values expressed as µmol trolox equivalents increased from 572±33 to 646±20 (increase=13%) following one week supplementation with the powerful direct antioxidant vitamin C whereas it remained stable (from 570±31 to 578±26, increase=1%) following one week supplementation with the composition according to the invention. Thus, the aforementioned composition did not modify the TAC score in subjects that where already well oxy-redox balanced whereas the direct antioxidant treatment produced a further increase that may lead to a reductive stress.

Advantageously, the composition according to the invention does not significantly modify the antioxidant capacity in subjects that already enjoy full efficiency of their antioxidant system, i.e. it does not induce signs of reductive stress as observed after the ingestion of direct antioxidants.

Example 4

A series of subjects virtually free from diseases where screened for their fasting blood Homocysteine and for their MTHFR and MTRR genotype. All those with a circulating Homocysteine higher than 12 µmol/l were offered a nutritional support with the composition formulated according to EXAMPLE 1, 1 tablet per day during 12 weeks. Fasting plasmatic Homocysteine was checked again at the end of the supplementation period. Out of 150 subjects screened, 37 had a fasting Homocysteine higher than 12 µmol/l, 9 of them where heterozygote for the C677T variant of MTHFR, 5 of them where heterozygote for the 12980 variant of MTHFR and 7 of them were heterozygote for the MTRR 66AG variant. The average baseline Homocysteine plasma concentration in the 37 treated subjects was 19.08±5.2 µmol/l and decreased to 10.5±3.4 µmol/l after the treatment. The subgroup of 21 subjects carrying a defective genetic variant decreased their Homocysteine from 22.1±4.6 to 12.3±3.2 µmol/l.

The composition according to the invention provides all the support needed to allow the metabolization of Homocysteine and may therefore lower the Homocysteine circulating concentration while also increasing its use for the production of active methyl groups in support to cell growth and differentiation and for the synthesis of GSH. Due to the content in methylated forms of both folic acid and cobalamin, this effect can be achieved also in subjects carrying a detective variant of the MTFHR and MTRR enzymes.

Advantageously, a daily ingestion of the composition according to the invention is used to obtain the reduction of the circulating Homocysteine both in subjects carrying standard genotypes of the MTHFR and MTRR and in those carrying the pathologic genetic variants of said enzymes.

Example 5

Mice embryos carrying the transgenic Agouti gene Avy will develop during gestation an Agouti-yellow color hair instead of the normal brown color proportionally to the lack of cytosine methylation at the relevant gene promoter. Mothers with a good DNA methylation function during early embryogenesis will generate offspring exerting less of the yellow color, thus the proportion of yellow color in the offspring can be used as a measure of efficiency of DNA methylation marking. Newborn mice are classified as Y0 to Y5 according to the amount of yellow phenotype, from Y0 for those without yellow hair up to Y5 in those fully colored in yellow. Dams of the inbred agouti mouse strain VY underwent diversified feeding during their gestation: their standard diet (n=10), or; their standard diet fortified with folic acid in amounts equivalent to a human dose of 400 µg daily (n=10), or; their standard diet fortified with the substances in amounts equivalent to a human dose of 1 tablet per day of the formulation of EXAMPLE 1 (n=10). The offspring was classified Y0 to Y5 according to the amount of yellow colour. In the standard diet group the rate of offspring abundant Agouti yellow color (Y3 to Y5) was 66%, which decreased to 45% in the offspring from folic acid supplementation and to 31% in the offspring supplemented by the composition according to the invention. This indicates that the composition exerted a preventive effect on the expression of the Agouti gene that was substantially higher that that provided by plain folic acid.

Besides their indirect antioxidant properties the compositions according to the invention also favor the transmethylation reactions and may improve the availability of active methyl groups for critical methylation processes including DNA and histone methylation as part of the cell genomic regulation. Moreover, the antioxidant properties are synergic in this improvement because they will prevent and/or revert the oxidation of already methylated cytosines and guanosines so to preserve the regulating properties of DNA bases methylation. This activity will reflect on the genetic and genomic stability of developing embryos of duly supplemented mothers and will be of help in preventing the occurrence of newborn diseases related to disturbances of these processes. Advantageously, the daily ingestion of the composition according to the invention by pregnant females is used to preserve the DNA and histone methylation marks so to prevent the occurrence of newborn diseases including NTDs and ASDs.

Example 6

Couples undergoing a planned pregnancy by means of Assisted Reproductive Technologies (ART) will be recruited for a prospective interventional clinical trial and randomised for the daily nutritional support with the composition formulated according to EXAMPLE 1, 1 tablet per day, versus no treatment. In the active intervention group both partners will assume the substances from the day of first referral to the ART clinic up to the occurrence of a confirmed clinical pregnancy. Thereafter, the pregnant women will continue the daily support with the composition according to the invention for further 3 months after the confirmation of the clinical pregnancy. The pregnancies from both the intervention and the control group will be monitored to record pregnancy losses, pregnancy diseases, pregnancy duration, delivery disturbances, birth weight and newborn malformations and diseases. Babies born from both the intervention and the control group will be followed up during five years after birth to detect the possible diagnosis of ASDs and of other childhood diseases.

Due to the positive effect on the quality of the gametes the pre-conceptional support, as described in EXAMPLE 6, the composition according to the invention has the potential to improve the fertility of the supplemented couples so to achieve increased pregnancy rates within ART cycles.

Example 7

One hundred couples resistant to at least 2 ART cycles were randomly assigned to the intervention group with both partners assuming daily 1 tablet of the composition formulated according to EXAMPLE 1 during 4 months before a new ART attempt (n=50), Matched couples that did not assume any treatment served as the control group. The intervention group recorded 27 clinical pregnancies (clinical pregnancy rate—CPR=54%) and 24 live births (live birth rate-LBR=48%) compared to 12 clinical pregnancies (CPR=24%) and 10 live births (LBR=20%) in the control group. Moreover, in the intervention group 16 out of 27 clinical pregnancies (59%) where achieved spontaneously, i.e. by natural conception occurring earlier than the planned ART cycle, whereas no spontaneous pregnancies were recorded in the control group.

The high rate of spontaneous pregnancies as recorded in EXAMPLE 7 vouches for a significant improvement of the fertility potential by natural route so that the composition according to the invention may be of help in improving the pregnancy rates also in couples seeking pregnancy by natural intercourses. In addition, couples doing so will have accomplished the first part of the peri-conceptional support intended for prevention of newborn diseases as described in EXAMPLE 6.

Example 8

Women referring to gynecology practices for pre-conception evaluations will be asked to enter, together with their partners, a prospective interventional clinical trial aimed to test the efficacy of the composition formulated according to EXAMPLE 1, 1 tablet per day for 12 months, or no treatment according to a randomization list. The CPR, the LBR and the time to pregnancy will be calculated and compared between groups.

Example 9

Forty women suffering from PCOS and with no ovulation during the previous 2 cycles were randomly assigned to a 3 months dietary support with 1 tablet daily of the composition formulated according to EXAMPLE 1, 1 tablet per day, or no treatment. Plasma homocysteine was evaluated at baseline and at the end of the treatment. The third treated cycle was monitored to check whether ovulation was occurring. Out of 18 women completing the treatment 13 (72%) had an ovulatory cycle during the third month of treatment and their blood homocysteine lowered from 15.5±3.5 µmol/l at baseline to 10.6±2.2 µmol/l after treatment. Among the 16 women in the control group that completed the 3 month follow-up only 5 (31%) had an ovulatory cycle with their plasma homocysteine remaining in the same range of concentration (14.0-±3.6 µmol/l) as compared to baseline (14.9±3.3 µmol/l).

Example 10

Thirty male patients newly diagnosed as affected by type 2 diabetes mellitus and starting a treatment with metformin, 1-2 gr daily, where randomly assigned to a 3-month adjuvant treatment with the composition formulated according to EXAMPLE 1, 1 tablet per day, or no treatment. Plasma homocysteine remained stable at the end of treatment in the patients receiving the adjuvant nutritional support (from 12.01±2.2 to 11.00±1.2 µmol/l) whereas it increased from 12.04±1.6 µmol/l at baseline to 14.4±2.1 µmol/l at the end of follow-up in the patients receiving only metformin indicating that the nutritional support had prevented the metformin-induced increase of Homocysteine. The serum HbA1C percentage decreased more in the group of patients receiving the nutritional support, from 10.3% to 8.1%, than in patients receiving metformin only, from 10.4% to 9.2%, indicating that the supplementation had also improved the glucose balance.

Example 11

Male patients with type 2 diabetes and well controlled with metformin (HbA1c<7%), 1 gram per day, were tested for the possible metformin substitution with the with the composition formulated according to EXAMPLE 1, 1 tablet per day. After one month of co-treatment with the dietary supplement the patients were asked to decrease their metformin to 500 mg per day and HbA1c was controlled again after 2 months. Those still having HbA1c<7% after this co-treatment were completely withdrawn metformin and checked again after 2 months of nutritional supplementation only. Out of 9 patients started. 7 of them still had HbA1c<7% after 2 months on half dose of metformin, 1 likely failed due to a very bad treatment compliance and 1 appeared to be a true non-responder, both were discontinued, Out of 7 completing the 2 months on dietary supplementation only, 6 were still well compensated after metformin withdrawal whereas 1 stepped back to the co-treatment with metformin 500 mg.

Advantageously, the daily ingestion of the composition according to the invention by patients with type 2 diabetes is used to achieve good glucose homeostasis without undergoing to pharmacologic treatments.

Example 12

Twenty women with spontaneous menopause from at least 6 months and referring due to the occurrence of menopausal vasomotor symptoms (Menopausal Rating Score-MRS more than 15 with a subscore 1 (hot flashes and sweats) of at least 2) were randomly assigned to a 3 month treatment with a phytoestrogen product from the market or with the composition formulated according to EXAMPLE 1, 1 tablet per day. MRS did not differ between groups at baseline. All patients received instructions to fill in a questionnaire to record the symptom evolution during the first week of treatment, follow-up visits were planned at 1 and 3 months after treatment start. During the first week of treatment 4 out of 10 patients receiving the dietary supplement were already symptom free at day 3 and another 4 the patients were symptom free at day 7 whereas none of the patients under phytoestrogens recorded significant improvements. At the 1 month follow-up 9 out of 10 under the dietary supplementation were symptom free compared to 3 out of 10 with partial improvements at the MRS in the phytoestrogen group. At the 3 month follow-up S out of 10 in the dietary supplement group were still symptom free whereas the other two had partial improvements of the MRS. Only S out of 10 patients in the phytoestrogen group had a partial improvement at the MRS including 4 new (late) responders whereas 2 early responders had stepped back to full symptomatology.

Advantageously, the daily ingestion of the composition according to the invention by ladies suffering from newly diagnosed vasomotor symptoms from menopause results in symptom remission in the majority of patients whereas the comparative treatment produces minor improvements in a minority of the patients.

Example 13

Six months aged APP23 transgenic mice, who develop early signs of Alzheimer disease due to over expression of the Amiloid Precursor Protein (APP), where fed with their standard diet or the substances in amounts equivalent to those listed in EXAMPLE 1 during one month. The Morris Water Maze (MWM) test was administered before and at the end of the trial period, Compared to baseline, mice assuming the composition according to the invention recorded a significant improvement at the hidden platform test on the trial day 4 with the latency to escape reduced from 31 to 14 seconds and with the swimming length before escaping reduced from 5.8 to 2.9 meters. The control animals fed with their standard diet recorded no changes or worsening.

Example 14

Subjects with an increased risk for cardiovascular events according to a Framingham Risk Score higher than 20% and with a fasting blood homocysteine higher than 15 µmol/l will be randomized for a nutritional support with the composition formulated according to EXAMPLE 1, 1 tablet per day, or no treatment. The enrolled subjects will be followed up during 5 years to detect the incidence of new events and their correlation with baseline and post-treatment Homocysteine levels.

High fasting plasma homocysteine is a well recognized risk factor for cardiovascular diseases due to its adverse effects on cardiovascular endothelium and smooth muscle cells with resultant alterations in subclinical arterial structure and function, even though intervention trials with B vitamins supplementation did not result in decreased cardiovascular mortality (Ganguly P. & Alam S F: *Role of homocysteine in the development of cardiovascular disease. Nutrition Journal* 2015, 4:6). Such lack of effect may be due to non-effective Homocysteine lowering by the tested interventions as well as to the occurrence of unknown associated risk factor that were not taken into account in such studies. As a matter of fact, due to the robust rationale and to the long list of added benefits, nutritional supports aimed at improving homocysteine metabolism remain a suitable option for individuals at increased risk of onset or relapse of cardiovascular diseases. Advantageously, the composition according to the invention can be assumed daily to decrease circulating homocysteine in subjects at increased risk of onset or relapse of cardiovascular diseases.

Example 15

Forty children (mean age 7 years and 3 months) previously diagnosed as affected by ASD by a developmental pediatrician or a pediatric neurologist were randomly assigned to a dietary supplementation with the composition according to the invention formulated in soluble granules and in half the daily amounts used in adults for 6 months versus no treatment. Symptoms were assessed at baseline and at the end of the intervention period by means of the Clinical Global Impression Scale-Improvement subscale as reported by the parents. The 18 children that completed the study out of 20 assigned to the active intervention reported significant improvements of verbal communication, attention and aggressiveness and border line improvements in mood and hyperactivity while the other symptoms did not change. All the symptoms were unchanged in the 15 children from the control group that completed the follow-up.

Example 16

Twenty adults (11 F-9 M) suffering from coeliac disease controlled with gluten-free diet and experiencing at least 3 acute relapses during the previous 12 months were randomly assigned to treatment with the composition formulated according to EXAMPLE 1, 1 tablet per day, or no treatment.

Patients were followed up for 6 months and acute coeliac disease relapses were recorded. During the observation period 7 out of 10 patients without the nutritional support experienced a disease relapse whereas no relapses occurred among the 10 patients receiving the support. This outcome may be interpreted as an effect of improved mucosal healing in patients receiving the dietary supplement: indeed, a healed mucosa may oppose a better barrier to the gluten antigens thereby limiting the inflammatory activation.

Advantageously, the compositions according to the invention can be used to prevent relapses of coeliac disease in patients under gluten free diet. Further advantageously, the possible improvement of the mucosal healing may favor faster healing during acute phases of the disease.

Example 17

Four non elite athletes trained for long distance running and under a standardised diet of the Mediterranean type were asked to run a 5 km distance at their semi-maximal pace after a 2-week supplementation with the composition formulated according to EXAMPLE 1, 1 tablet per day, and after no treatment according to a cross-over design (2-week wash out period). Their running time and their pre-exercise and post-exercise blood homocysteine were recorded. When performing after no treatment the mean (SD) homocysteine level increased from 12.05 (0.87) to 15.62 (1.29) µmol/L and the mean time (SD) to cover the distance was 19 minutes and 32 seconds (0:36). The same performance after dietary supplementation did not substantially change their blood homocysteine, from 11.8 (1.1) to 12.25 (1.2) µmol/L, while the time to distance decreased by an average of 18 seconds to 19:14 (0:27).

Advantageously, the daily ingestion of the composition according to the invention by ladies suffering from newly diagnosed vasomotor symptoms from menopause results in symptom remission in the majority of patients whereas the comparative treatment produces minor improvements in a minority of the patients.

Example 18

Bovine cumulus-oocyte complexes (COC) were obtained from the ovaries of slaughtered cows. COCs were aspirated from antral follicles (3-8 mm in diameter) and oocytes with at least four layers of cumulus cells with homogenous cytoplasm were selected. A sample of COCs was used to check the nuclear maturation stage at time of sampling (n=30). Control COCs were matured in vitro using 500 µL of TCM199 medium (Gibco; Invitrogen Co., Grand Island, N.Y., USA) supplemented with FSH and hCG and with 10% (v:v) calf serum (N=30). Sibling bovine COC were cultured with the same medium further supplemented with 100 µL of a solution containing the composition formulated according to EXAMPLE 1 where the amount of substances equivalent to a daily human dose had been diluted in 1 L (n=30). Out of 30 COCs tested at time of sampling, 28 were at GV stage, 2 at intermediate stage and none was at MII stage. After 24 hours of in vitro culture without the composition supplementation, out of 30 COCs cultured. 7 were still GV, 4 were intermediate and 19 had matured to the MII stage. After 24 hours of in vitro culture with the add-on of the composition, out of 30 COCs, 2 were still at GV stage, 2 were intermediate and 26 had matured to MII (+23% compared to controls), After in vitro fertilization of the MII oocytes obtained from the previous experiment 6/19 (32%) MII oocytes from the unsupplemented culture reached the blastocyst stage compared to 15/26 (58%) of MII oocytes that had been supplemented with the composition.

Advantageously, the in vitro supplementation of the culture medium with a solution containing the composition listed in EXAMPLE 1 results in an increased rate of in vitro maturation of ex-vivo oocytes and in a higher rate of blastocyst development. Further advantageously, the same type of supplementation may also benefit in vitro culture of embryos obtained from naturally matured oocytes and of stem cells.

The invention claimed is:

1. A composition comprising:
    a) methyl-tetra-hydrofolate and/or a pharmaceutically acceptable salt thereof in an amount between 100 and 800 µg of folic acid equivalents;
    b) methylcobalamin and/or the pharmaceutically acceptable salts thereof in an amount between 0.5 and 10 µg of cyanocobalamin equivalents;
    c) at least two vitamins B selected among vitamin B2, nicotinamide, vitamin B3 and vitamin B6 and/or the pharmaceutically acceptable salts thereof in an amount between 0.4 µg and 40 mg;
    d) a betaine and/or the pharmaceutically acceptable salts thereof in an amount between 100 and 2000 mg;
    e) a chelated zinc compound in an amount between 5 and 50 mg of zinc equivalents; and
    f) a cysteine derivative in an amount between 100 and 2000 mg,
    wherein the composition does not contain any antioxidant agent.

2. The composition according to claim 1, wherein vitamin B3 or nicotinamide is present in an amount between 4 and 40 mg.

3. The composition according to claim 1, wherein vitamin B2 is present in an amount between 0.4 and 5 mg.

4. The composition according to claim 1, wherein vitamin B6 is present in an amount between 0.4 and 5 mg.

5. The composition according to claim 1, wherein the betaine is trimethylglycine.

6. The composition according to claim 1, wherein the chelated zinc compound is selected from the group consisting of zinc amino acid chelate, zinc arginate, zinc ascorbate, zinc aspartate, zinc bisglycinate, zinc caprylate, zinc cysteinate, zinc ethanolamine phosphate, zinc fumarate, zinc glutamate, zinc glycinate, zinc histidinate, zinc ketoglutarate, zinc lysinate, zinc malate, zinc methionate, zinc orotate, zinc picolinate, zinc pidolate, zinc proteinate, zinc succinate, zinc tartrate, zinc taurate and zinc undecyclinate.

7. The composition according to claim 1, wherein the cysteine derivative is L-cystine or N-acetylcysteine.

8. The composition according to claim 1, comprising:
    a') L-5-methyltetrahydrofolate in an amount between 100 and 800 µg of folic acid equivalents;
    b'1) vitamin B3 or nicotinamide in an amount between 4 and 40 mg;
    b'2) vitamin B2 in an amount between 0.4 and 5 mg;
    b'3) methylcobalamin in an amount between 0.5 and 10 µg of cyanocobalamin equivalents;
    b'4) pyridoxine or pyridoxine hydrochloride in an amount between 0.4 and 5 mg;
    c') trimethylglycine or trimethylglycine hydrochloride in an amount between 100 and 2000 mg;
    d') zinc bisglycinate in an amount between 5 and 50 mg of zinc equivalents; and
    e') L-cystine in an amount between 100 and 2000 mg.

9. The composition according to claim 1, in the form of tablet, capsule, granule, soluble granule, drinkable solution, injection or suppository.

10. The composition according to claim 1, further comprising at least one physiologically acceptable excipient.

11. The composition according to claim 10, wherein the physiologically acceptable excipient is selected from the group consisting of bulking agents, anticaking agents, stabilizers and a mixture thereof.

12. An in vitro culture composition according to claim 1, in a form of liquid medium.

13. A composition comprising:
   a) methyl-tetra-hydrofolate and/or a pharmaceutically acceptable salt thereof in an amount between 150 to 600 µg of folic acid equivalents;
   b) methylcobalamin and/or the pharmaceutically acceptable salts thereof in an amount between 1.5 to 5 µg of cyanocobalamin equivalents;
   c) at least two vitamins B selected among vitamin B2, nicotinamide, vitamin B3 and vitamin B6 and/or the pharmaceutically acceptable salts thereof in an amount between 1.5 µg to 32 mg;
   d) a betaine and/or the pharmaceutically acceptable salts thereof in an amount between 150 to 1000 mg;
   e) a chelated zinc compound in an amount between 6 to 20 mg of zinc equivalents; and
   f) a cysteine derivative in an amount between 150 to 1000 mg.

14. The composition according to claim 13, wherein vitamin B3 or nicotinamide is present in an amount between 8 to 32 mg.

15. The composition according to claim 13, wherein vitamin B2 is present in an amount between 1 to 2 mg.

16. The composition according to claim 13, wherein vitamin B6 is present in an amount between 1 to 2 mg.

17. A composition comprising:
   a') L-5-methyltetrahydrofolate in an amount between 150 to 600 µg of folic acid equivalents;
   b'1) vitamin B3 or nicotinamide in an amount between 8 to 32 mg;
   b'2) vitamin B2 in an amount between 1 to 2 mg;
   b'3) methylcobalamin in an amount between 1.5 to 5 µg of cyanocobalamin equivalents;
   b'4) pyridoxine or pyridoxine hydrochloride in an amount between 1 to 2 mg;
   c') trimethylglycine or trimethylglycine hydrochloride in an amount between 150 to 1000 mg;
   d') zinc bisglycinate in an amount between 6 to 20 mg of zinc equivalents;
   e') L-cystine in an amount between 150 to 1000 mg.

* * * * *